(12) United States Patent
Berndl et al.

(10) Patent No.: US 7,906,144 B1
(45) Date of Patent: Mar. 15, 2011

(54) SOLUBILIZING AIDS IN POWDER FORM FOR SOLID PHARMACEUTICAL PRESENTATION FORMS

(75) Inventors: Gunther Berndl, Herxheim (DE); Jörg Breitenbach, Mannheim (DE); Folker Ruchatz, Neustadt (DE); Axel Sanner, Frankenthal (DE); Heinrich Sack, Haßloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 179 days.

(21) Appl. No.: 09/937,313

(22) PCT Filed: Oct. 5, 2000

(86) PCT No.: PCT/EP00/02382
§ 371 (c)(1), (2), (4) Date: Sep. 24, 2001

(87) PCT Pub. No.: WO00/57855
PCT Pub. Date: Oct. 5, 2000

(30) Foreign Application Priority Data

Mar. 25, 1999 (DE) .................................. 199 13 606

(51) Int. Cl.
*A61K 9/14* (2006.01)
*A61K 9/50* (2006.01)

(52) U.S. Cl. .................. 424/489; 424/499; 424/502

(58) Field of Classification Search .......... 424/437, 424/473, 486, 451, 484, 94.1, 9.8, 9.5, 94.6, 424/491, 499, 9.6, 95.6, 484.9, 4.1, 95.5, 489, 502; 264/5; 525/27

See application file for complete search history.

(56) References Cited

U.S. PATENT DOCUMENTS

| | | | | |
|---|---|---|---|---|
| 4,127,422 A * | 11/1978 | Guzi et al. | ...... | 524/47 |
| 4,259,315 A * | 3/1981 | Lippmann et al. | ...... | 424/37 |
| 4,778,816 A | 10/1988 | Abe et al. | ...... | 514/381 |
| 4,806,358 A * | 2/1989 | Khan et al. | ...... | 424/466 |
| 5,006,346 A * | 4/1991 | Edgren et al. | ...... | 424/473 |
| 5,264,222 A * | 11/1993 | Groenendaal et al. | ...... | 424/451 |
| 5,618,560 A * | 4/1997 | Bar-Shalom et al. | ...... | 424/486 |
| 5,670,158 A * | 9/1997 | Davis et al. | ...... | 424/400 |
| 5,741,524 A * | 4/1998 | Staniforth et al. | ...... | 424/489 |
| 5,834,472 A | 11/1998 | Sangekar et al. | ...... | 514/252 |
| 5,840,769 A * | 11/1998 | Kolter et al. | ...... | 514/781 |
| 5,853,698 A * | 12/1998 | Straub et al. | ...... | 424/9.52 |
| 5,858,412 A * | 1/1999 | Staniforth et al. | ...... | 424/489 |
| 5,993,805 A * | 11/1999 | Sutton et al. | ...... | 424/94.1 |
| 6,011,096 A * | 1/2000 | Shih et al. | ...... | 524/99 |
| 6,063,865 A * | 5/2000 | Ball et al. | ...... | 525/57 |
| 6,066,334 A * | 5/2000 | Kolter et al. | ...... | 424/465 |
| 6,086,915 A * | 7/2000 | Zeligs et al. | ...... | 424/455 |

FOREIGN PATENT DOCUMENTS

| | | |
|---|---|---|
| DE | 35 30 780 | 7/1986 |
| EP | 0 729 748 | 9/1996 |
| WO | WO 93/11749 | 6/1996 |

* cited by examiner

*Primary Examiner* — Michael G Hartley
*Assistant Examiner* — Micah-Paul Young
(74) *Attorney, Agent, or Firm* — Novak Druce + Quigg LLP

(57) ABSTRACT

The invention relates to excipients in powder form for use in solid pharmaceutical presentations, comprising a pharmaceutically acceptable polymer and a liquid or semisolid solubilizing surface-active substance.

13 Claims, No Drawings

SOLUBILIZING AIDS IN POWDER FORM FOR SOLID PHARMACEUTICAL PRESENTATION FORMS

The present invention relates to excipients in powder form with high density of loading with solubilizing surface-active substances for use in solid pharmaceutical presentations, comprising a pharmaceutically acceptable polymer and a liquid or semisolid solubilizing surface-active substance.

The rate of dissolution of many active ingredients of low solubility in water can be increased by mixing with polymers such as, for example, polyvinylpyrrolidone. The mixing can take place for example by trituration, melt extrusion of polymer/active ingredient mixtures, coprecipitation, spray-drying of polymer/active ingredient solutions or granulation of active ingredient/polymer mixtures in a fluidized bed or by wet extrusion. However, the rate of dissolution and the bioavailability of such polymer/active ingredient mixtures is often inadequate.

It is generally known that the rate of dissolution and the bioavailability can be increased by adding a surface-active substance.

For example, U.S. Pat. No. 5,834,472 discloses that it is possible to increase the bioavailability of a specific antifungal agent by use of a nonionic surface-active substance.

WO 93/11749 describes a process for producing solid dispersions of active ingredients of low solubility in water, in which firstly the active ingredient and polymeric carrier are mixed, and this mixture is then granulated with a solution of a surface-active substance in a fluidized bed. The resulting granules are then extruded using an extruder with a heating zone, followed by grinding and processing to drug forms.

However, many surface-active substances with solubilizing properties are liquid or semisolid. Solubilizers of these types are generally employed in formulations intended to be used for filling hard or soft gelatin capsules, or in solutions for intravenous or oral administration.

However, the use of such solubilizers in amounts of more than 10% by weight, based on the tablet weight, which are relevant for solubilizing active ingredients of low solubility gives rise, because of the waxy consistency, to problems concerning the processability of the formulations.

It is an object of the present invention to find a procedure which permits larger amounts of liquid or semisolid solubilizing surface-active substances to be employed without disadvantages for the processing technique.

We have found that this object is achieved by an excipient in powder form, comprising a pharmaceutically acceptable polymer and more than 10 and up to 50% by weight, preferably 15 to 40% by weight, particularly preferably 20 to 30% by weight, based on the total amount of the excipient, of a liquid or semisolid solubilizing surface-active substance.

Liquid or semisolid means for the purpose of this invention that the surface-active substance is liquid at 20° C. or has a drop point in the range from 20 to 60° C., preferably 20 to 50° C., particularly preferably 20 to 40° C. The surface-active substance preferably has an HLB (hydrophilic lipophilic balance) in the range from 2 to 18, particularly preferably from 10 to 15.

A compound from the following nonionic classes is suitable as surface-active substance:
Polyoxyethylene/polyoxypropylene block copolymers (poloxamers)
Polyethylene glycols with average molecular weights in the range from 300 to 6000
Saturated and unsaturated polyglycolized glycerides like those known, for example, under the brand names Gelucire® or Labrafil® semisynthetic glycerides, fatty acid esters or ethers of fatty alcohols Those particularly suitable are thus ethoxylated sorbitan fatty acid esters such as, for example, polyoxyethylene 20 sorbitan monolaurate, polyoxyethylene 20 sorbitan monopalmitate, polyoxyethylene 20 sorbitan monostearate, polyoxyethylene 20 sorbitan monooleate, polyoxyethylene 20 sorbitan tristearate, polyoxyethylene 20 sorbitan trioleate, polyoxyethylene 4 sorbitan monostearate, polyoxyethylene 4 sorbitan monolaurate or polyoxyethylene 4 sorbitan monooleate.

Also suitable are sorbitan fatty acid esters such as, for example, sorbitan monolaurate.

Preferred solubilizers are products of the reaction of varying amounts of ethylene oxide with castor oil, hydrogenated castor oil or 12-hydroxystearic acid, for example polyoxyethylene glycerol ricinoleate 35, polyoxyethylene glycerol trihydroxystearate or PEG 660-12-hydroxystearate (polyglycol ester of 12-hydroxystearic acid with 30 mol % of ethylene glycol).

Macrogol 6 cetylstearyl ether or macrogol 25 cetylstearyl ether are likewise suitable.

Particularly suitable pharmaceutically acceptable polymeric carrier materials for the excipient according to the invention are water-soluble polymers. Preference is given to homo- or copolymers of N-vinylpyrrolidone with Fikentscher K values of from 12 to 100, preferably 17 to 30, for example polyvinylpyrrolidone, copolymers with vinyl acetate or vinyl propionate such as, for example, copovidone (VP/VAc-60/40).

Also suitable are polyvinyl alcohol, and polyvinyl acetate which may also be partly hydrolyzed. Acrylate polymers of the Eudragit type are likewise suitable.

Suitable polymers are also cellulose derivatives such as alkyl-celluloses, hydroxyalkylcelluloses or hydroxyalkylcelluloses, for example ethylcellulose or hydroxypropylcellulose.

The excipients can be produced in various ways. Thus, for example, the solubilizer can be added to a solution of the polymer, and the solvent can then be removed. Suitable solvents are, in particular, water, but also ethanol or longer-chain alcohols such as isopropanol, propanol, butanols or else acetone or mixtures of such solvents. Spray-drying is the preferred drying process.

The excipients can also be produced by granulation processes known per se, such as, for example, fluidized bed granulation, in which case a liquid phase containing the solubilizer is sprayed onto the solid carrier.

The excipients in powder form can also be produced by melt extrusion in the absence of solvents. During the melt extrusion, the liquid solubilizer phase can be metered into the extruder continuously or batchwise. The melt thus obtained can be processed to powders in various ways.

Thus, the extrudate emerging through a die or breaker plate can be granulated by conventional techniques, in particular the hot-cup technique, and, where appropriate, also ground. The melt can also be extruded through the open extruder head, likewise resulting in pellets. The solubilizer-containing excipient can also be compressed to tablets by calendering and then be ground. The grinding may additionally take place in the extruder, or granulation can take place in so-called roll mills.

If desired, the solubilizer-containing powders according to the invention may also comprise other excipients, for example flow regulators, dyes, mold release agents, fats and waxes, disintegrants, bulking agents and other conventional tableting excipients such as, for example, sugars, sugar alcohols or starch degradation products.

The powders according to the invention are free-flowing and preferably have particle sizes of from 10 to 1000μ.

They can be processed without restriction for producing solid forms which can be administered orally, such as tablets, microtablets, sachet fillings, effervescent tablets, suckable tablets, pellets or pastilles. Such forms can be produced by conventional pharmaceutical processes such as melt extrusion, tableting by compression or paste extrusion with subsequent shaping.

The powders according to the invention are suitable in principle for formulations of all pharmaceutical, cosmetic or dietary active ingredients. It is particularly suitable for formulations of CNS-active substances, dihydropyridine derivatives, protease inhibitors, reverse transcriptase inhibitors, antimycotics or cytostatics.

A particular advantage of the powders according to the invention is also that other liquid substances such as, for example, oils can be incorporated into the excipient in powder form and then lead, especially in the case of oil-soluble active ingredients, to an improvement in the bioavailability.

EXAMPLES

Example 1

1.65 l of a 20% strength aqueous solution (m/V) of Cremophor RH 40 (product of the reaction of 1 mol of hydrogenated castor oil with 45 mol of ethylene oxide) were stirred at room temperature into 5 l of a 20% strength aqueous solution (m/V) of polyvinylpyrrolidone with a K value of 30 (Kollidon 30). The solution resulting from this was then spray-dried to result in a fine powder.

Example 2

2 kg/h of a copolymer of 60% by weight of vinylpyrrolidone and 40% by weight of vinyl acetate with a K value of 30 were metered by means of a weigher into a twin screw extruder (ZSK 30 Werner & Pfleiderer). At the same time, molten Cremophor RH 40 was continuously metered into section 3 of the extruder by pump at a rate of 0.5 kg/h. The mixture was homogenized and plastified in the extruder and then calendered.
Temperatures [° C.]: 30 78 120 109 110 110
Die [° C.]: 103
Vacuum: 80 mbar The calendered moldings were ground using a ring sieve mill from Retsch (2 mm sieve).
Tableting 50% by weight of the resulting powder were compressed with 10% by weight of crospovidone, 10% by weight of Ca silicate, 8.5% by weight of microcrystalline cellulose, 20% by weight of cyclosporin, 0.5% by weight of Mg stearate and 1% by weight of Aerosil (highly dispersed silica) to give 500 mg tablets.

Example 3

A copolymer of 60% by weight of vinylpyrrolidone and 40% by weight of vinyl acetate with a K value of 30 was metered at 2 kg/h by means of a weigher into a twin screw extruder (ZSK 30 Werner & Pfleiderer). At the same time, molten Cremophor RH 40 mixed with 20% by weight of corn oil was metered continuously into section 3 of the extruder by pump at a rate of 0.5 kg/h. The mixture was homogenized and plastified in the extruder and then calendered. The finished mixture contained:
80% by weight of Kollidon VA 64 (copovidon)
16% by weight of Cremophor RH 40
4% by weight of corn oil
Temperatures [° C.]: 30 70 115 105 105 105
Die [° C.]: 103
Vacuum: 80 mbar

We claim:

1. A process for producing an excipient adapted for use in a solid pharmaceutical dosage form, wherein said excipient is in the form of a free-flowing powder and consists essentially of:
   a pharmaceutically acceptable polymer, wherein the polymer is a homo- or copolymer of N-vinylpyrrolidone, which is a water-soluble polymer with Fikentscher K values of from 12 to 100, and
   from 10 to 50% by weight, based on the total weight of said excipient, of a liquid or semisolid solubilizing surface-active substance, comprising ethoxylated sorbitan fatty acid esters, or the products of the reaction of ethylene oxide with castor oil, hydrogenated castor oil or with 12-hydroxystearic acid,
said process comprising either:
   spray-drying a solution comprising the surface-active substance and the pharmaceutically acceptable polymer, or
   processing the polymer and the surface-active substance in an extruder to obtain a homogeneous melt and subsequently converting the melt into the free-flowing powder.

2. The process according to claim 1, wherein the excipient comprises a surface-active substance which has a drop point in the range from 20 to 40° C.

3. The process according to claim 1, wherein the excipient comprises a surface-active substance which has an HLB of from 10 to 15.

4. The process according to claim 1, wherein the excipient comprises from 15 to 40% by weight of the surface-active substance.

5. The process according to claim 1, wherein the excipient comprises ethoxylated sorbitan fatty acid esters as surface-active substances.

6. The process according to claim 1, wherein the excipient comprises the products of the reaction of ethylene oxide with castor oil, hydrogenated castor oil or with 12-hydroxystearic acid as surface active substance.

7. The process according to claim 1, wherein the excipient comprises from 20 to 30% by weight of the surface-active substances.

8. The process according to claim 1, wherein the excipient is in the form of a free-flowing powder of particles having a particle size of from 10 to 1000μ.

9. The process according to claim 1, wherein the surface-active substance of the excipient is a non-ionic compound.

10. The process of claim 1, wherein said excipient is free of pigment.

11. A process for producing a free-flowing powder excipient for use in a solid pharmaceutical dosage form consisting essentially of:
   a pharmaceutically acceptable polymer, and
   from 10 to 50% by weight, based on the total weight of the excipient, of a liquid or semisolid solubilizing surface-active substance, wherein
      the pharmaceutically acceptable polymer in the excipient is a homo- or copolymer of N-vinylpyrrolidone, and is a water-soluble polymer with Fikentscher K values of from 12 to 100 the process comprising producing the free-flowing powder excipient by one of:

spray-drying a solution comprising the surface-active substance and the pharmaceutically acceptable polymer, or extruding the polymer and the surface-active substance to obtain a homogeneous melt and subsequently converting the melt into the free-flowing powder, wherein the surface active substance is in a suitable concentration to keep the excipient free flowing.

12. The process of claim 11, wherein the concentration of surface active substance is 15 to 40% by weight based on the weight of the excipient.

13. The process of claim 11, wherein the concentration of surface active substance is 20 to 30% by weight based on the weight of the excipient.

* * * * *

UNITED STATES PATENT AND TRADEMARK OFFICE
CERTIFICATE OF CORRECTION

| | | |
|---|---|---|
| PATENT NO. | : 7,906,144 B1 | |
| APPLICATION NO. | : 09/937313 | |
| DATED | : March 15, 2011 | |
| INVENTOR(S) | : Berndl et al. | |

It is certified that error appears in the above-identified patent and that said Letters Patent is hereby corrected as shown below:

The PCT Filing Date item (22) on the cover of the patent should read:
"March 17, 2000" instead of >October 05, 2000<

Signed and Sealed this
Seventeenth Day of May, 2011

David J. Kappos
*Director of the United States Patent and Trademark Office*